United States Patent [19]

Nedungadi et al.

[11] Patent Number: 5,713,939

[45] Date of Patent: Feb. 3, 1998

[54] DATA COMMUNICATION SYSTEM FOR CONTROL OF TRANSCUTANEOUS ENERGY TRANSMISSION TO AN IMPLANTABLE MEDICAL DEVICE

[75] Inventors: Ashok P. Nedungadi, Lake Oswego, Oreg.; Xintao Wang, Houston, Tex.

[73] Assignee: Sulzer Intermedics Inc., Angleton, Tex.

[21] Appl. No.: 714,449

[22] Filed: Sep. 16, 1996

[51] Int. Cl.[6] ............................ A61B 5/02; A61N 1/08; A61N 1/378
[52] U.S. Cl. ...................... 607/33; 607/29; 607/899
[58] Field of Search ........................... 607/5, 33, 55–57, 607/29; 128/899

[56] References Cited

U.S. PATENT DOCUMENTS

| | | |
|---|---|---|
| 3,195,540 | 7/1965 | Waller . |
| 3,454,012 | 7/1969 | Raddi .................................. 607/33 |
| 3,824,129 | 7/1974 | Fagan . |
| 3,865,101 | 2/1975 | Saper et al. ........................ 607/5 |
| 3,867,950 | 2/1975 | Fischell ............................. 607/33 |
| 3,888,260 | 6/1975 | Fischell ............................. 607/36 |
| 3,942,535 | 3/1976 | Schulman .......................... 607/33 |
| 4,014,346 | 3/1977 | Brownlee et al. ................. 607/33 |
| 4,082,097 | 4/1978 | Mann et al. ....................... 607/33 |
| 4,096,856 | 6/1978 | Smith et al. ....................... 607/5 |
| 4,096,866 | 6/1978 | Fischell ............................. 607/33 |
| 4,134,408 | 1/1979 | Brownlee et al. ................. 607/33 |
| 4,166,470 | 9/1979 | Neumann .......................... 607/33 |
| 4,172,459 | 10/1979 | Hepp ................................. 128/697 |
| 4,232,679 | 11/1980 | Schulman .......................... 607/33 |
| 4,275,739 | 6/1981 | Fischell ............................. 607/9 |
| 4,323,075 | 4/1982 | Langer .............................. 607/5 |
| 4,432,363 | 2/1984 | Kakegawa ......................... 607/33 |
| 4,548,209 | 10/1985 | Wielders et al. .................. 607/4 |
| 4,635,639 | 1/1987 | Hakala et al. ..................... 607/4 |
| 4,661,107 | 4/1987 | Fink .................................. 607/33 |
| 4,665,896 | 5/1987 | LaForge et al. ................... 623/3 |
| 4,700,707 | 10/1987 | Batina et al. ..................... 607/32 |
| 4,787,389 | 11/1988 | Tarjan ............................... 607/4 |
| 4,827,936 | 5/1989 | Pless et al. ....................... 607/4 |
| 4,903,699 | 2/1990 | Baker, Jr. et al. ................ 607/9 |
| 5,279,292 | 1/1994 | Baumann et al. ................. 607/57 |
| 5,314,453 | 5/1994 | Juetter ............................... 607/61 |
| 5,350,413 | 9/1994 | Miller ................................ 607/61 |
| 5,411,537 | 5/1995 | Munshi et al. .................... 607/33 |
| 5,562,595 | 10/1996 | Neisz . | |

OTHER PUBLICATIONS

*A Modular Expandable Implantable Temperature Biotelemeter*, IEEE Transactions on Biomedical Engineering, vol. BME–27, No. 5, pp. 242–248, May 1980.

*Controlled External Powering of Miniaturized Chronically Implanted Biotelemetry Devices;* IEEE Transactions on Biomedical Engineering, vol. BME–23, No. 2., pp. 124–129, Mar. 1976.

*Controlled Transcutaneous Powering of a Chronically Implanted Telemetry Device;* Biotelemetry Patient Monitg 6: 176–185 (1979).

*Passive Biotelemetry by Frequency Keying;* IEEE Transactions on Biomedical Engineering, vol. BME.

Chapter 4 ("*Tachyarrhythmia Sensing and Detection*"); of Implantable Cardioverter Defibrillator; Publisher: Futura Publishing Company, Inc.; 1994.

*Primary Examiner*—Marvin M. Lateef
*Assistant Examiner*—Carl H. Layno
*Attorney, Agent, or Firm*—John R. Merkling

[57] ABSTRACT

A data communication system for control of transcutaneous energy transmission to an implantable medical device is disclosed having an implantable medical device with rechargeable batteries and a single coil that is employed both for energy transmission and data telemetry. Control circuitry in the implantable device senses battery voltage and current through the battery, encodes those values by use of a multiplexer, and transmits the sensed and encoded values through the coil to an external energy transmission device. The external device includes a coil that is electromagnetically coupled to the coil in the implantable device for receiving the encoded signals and for transmitting energy to the implantable device. The external device decodes the transmitted values and transmits those to a controller for controlling energy transmission.

49 Claims, 6 Drawing Sheets

FIG. 6
COUNTER 118
PULSE GENERATOR 176
COIL 32
EDGE DETECTOR 158 (I/V)
EDGE DETECTOR 158 (C)
FIG. 7
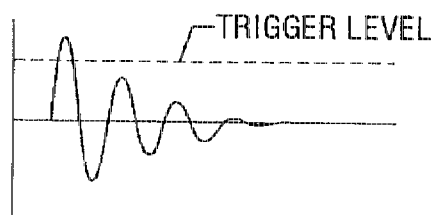
TRIGGER LEVEL

DATA COMMUNICATION SYSTEM FOR CONTROL OF TRANSCUTANEOUS ENERGY TRANSMISSION TO AN IMPLANTABLE MEDICAL DEVICE

BACKGROUND OF THE INVENTION

1. Field of the Invention

The present invention relates to implantable medical devices. More specifically, the present invention relates to battery-powered implantable devices that receive energy for recharging the battery from an external transcutaneous energy transmitter. Still more specifically, the invention relates to a telemetry system for transmitting data from the implantable medical device to the external energy transmitter for controlling the energy transmission.

2. Description of the Relevant Art

Implantable medical devices, such as pacemakers and defibrillators, typically operate from battery power. Traditionally, disposable batteries including zinc-mercuric oxide cells were used. Because of problems associated with high self-discharge, hydrogen gas evolution, and limited life, other power sources were investigated. In recent years, implantable devices have been powered by rechargeable batteries. Such power systems solved many of the problems associated with prior power sources, but suffer from their own shortcomings.

The operational life of an implanted device has been extended by the use of rechargeable batteries. Whereas operational life of an implanted device incorporating a disposable battery was limited to the duration of the battery charge, implanted devices using rechargeable batteries can function for significantly longer periods given that the batteries can be repeatedly recharged. Further, transcutaneous energy transmissions ("TET") charging techniques, such as that disclosed in U.S. Pat. No. 5,411,537, allow non-invasive battery charging.

TET charging systems transmit energy from a device external to the patient's body to an implanted device using the principle of mutual induction. Alternating current in an external primary coil induces electrical energy through the patient's skin and body tissues to a secondary coil in the implanted device. The current in the secondary coil is then rectified and used to charge the implanted device's battery.

Early battery charging schemes merely charged the battery with a constant energy source with little, if any, charge control. Such charging systems proved unsatisfactory because they failed to detect when the battery was fully charged, and thus failed to remove the charging current or indicate the end of charge condition. Overcharging a battery can damage the battery, thereby critically impairing its usability. Therefore, more sophisticated control systems were developed to indicate and respond to the end of the charge condition. Such systems monitored any one of a number of battery parameters such as current, voltage, and temperature, and turned off the charging current when the battery was fully charged. To accomplish this control, conventional charging systems must be provided with a means to ascertain battery and/or charging conditions, and control parameters for comparing against the sensed values to determine when to terminate charging to protect the battery and the circuitry of the implantable device.

For these reasons, TET systems should be designed to detect when the implanted rechargeable battery becomes fully charged. Because TET chargers are external devices and include no physical connection to the implanted device, telemetry schemes are used to transmit battery and charging information from the implanted device to the external TET charger.

Data telemetry also is used for purposes other than for transmitting charging information. For example, many implantable devices contain sensors for monitoring physiological parameters such as heart rate, body temperature, and oxygen saturation level. Output signals from these physiological sensors are used by the implanted medical device to assist the device in delivering proper medical treatment. It is often beneficial to health care providers to monitor physiological conditions regarding the implanted device. Accordingly, data telemetry may be advantageous to transmit physiological parameters from the implemented device to an external unit for use by the health care provider.

Numerous and sometimes competing concerns affect implantable device design. For example, minimizing size, weight, and power consumption dictate the use of specific parts and materials. Achieving minimal size, weight, and power consumption is frustrated by the need to incorporate data telemetry circuitry in a device that may already be crowded with other components and circuits. For example, prior art implantable devices that employed data telemetry systems have generally employed two separate coils in the implanted device, one for energy transmission and a second for data telemetry. This increases the size, weight and cost of the implantable device.

The use of separate coils for energy transmission and data telemetry has additional undesirable consequences arising from the need to align simultaneously the two coils in the implantable device with the two corresponding coils in the TET device. Proper and precise alignment affects the charging efficiency. If the energy transmission coils are not closely aligned, charging efficiency decreases significantly. The losses during charging manifest themselves as heat in the implantable device causing the temperature of the device to rise. An elevation in temperature of only a few degrees may damage the tissue surrounding the device. Also, for efficient data transmission, the coils responsible for that function should be closely aligned. As can be appreciated, problems associated with providing proper alignment are compounded in systems where two sets of coils must be aligned. Additionally, prior art systems employing two sets of coils also tended to suffer from undesirable mutual coupling between the energy and data coil pairs. Further, some prior art control systems were not able to detect cardiac arrhythmias and stop charging. It is desirable to detect such arrhythmias and to discontinue charging during such occurrences.

Accordingly, it would be advantageous to have an implantable device that implements transcutaneous energy transmission for recharging the device's batteries that minimizes size, weight, and power consumption by minimizing the number of parts. Further, it would be desirable to implement a TET based implantable device that avoids mutual coupling problems and coil alignment problems experienced by prior art systems that have employed separate sets of coils for energy transmission and data telemetry. Also, because complex systems are more difficult and costly to test and manufacture, it is desirable to have simpler designs.

SUMMARY OF THE INVENTION

The present invention provides a data communication system for the control of transcutaneous energy transmission to an implantable medical device from an external energy transmitter. The invention includes an implantable medical device having a battery capable of being recharged from a transcutaneous energy transmission device, and having a coil selectively coupled to said battery via a switch for receiving energy from the transcutaneous energy transmission device. A current sensor in the implantable device is coupled to the battery for detecting the current flowing through the battery and for providing an output signal indicative of the current level. The implantable device further includes multiplexing circuitry coupled to the battery for detecting voltage of the battery and for receiving a current signal from the current sensor and generating a signal indicative of either the amount of current through the battery or the voltage of the battery. The implantable device further includes output circuitry for receiving the signal from the multiplexing circuitry and selectively opening and closing the switch to transmit encoded signals through the coil to the external transcutaneous energy transmitter that are indicative of the amount of current through the battery and the voltage of the battery.

The invention further includes a transcutaneous energy transmission system for recharging a battery in an implantable medical device and for controlling the energy transfer based upon signals generated in the implantable device that indicate the battery's state of charge of discharge. The system includes an external energy transmission device having a coil, a current sensor for sensing current through the coil, and detection circuitry for detecting encoded signal received from the implantable medical device. The implantable device includes a rechargeable battery, a coil for coupling to the coil in the external device, and charging control circuitry for sensing the amount of current flowing through the battery and the battery voltage, encoding those sensed values, and transmitting them through the coils to the external energy transmission device in order to control the transcutaneous energy transmission. The charging and control circuitry in the implantable device includes a switch coupling the coil to the battery, a current sensor for detecting and providing an output signal indicative of the current flowing through the battery, and a multiplexer for detecting the voltage of the battery and receiving the output signal from the current sensor and generating a signal indicating either the amount of current through the battery or the voltage of the battery. The charging control circuitry further includes output circuitry coupled to the multiplexing circuitry for encoding the voltage and current values sensed and transmitting them through the coil of the implantable device to the external energy transmission device where the signals are received and decoded such that the energy transmission can be controlled.

In this manner, the present invention comprises a combination of features and advantages which enable it to substantially advance the art associated with implantable medical devices and, in particular, transcutaneous energy transmission systems. The invention provides data telemetry and energy transmission transcutaneously by means of a single pair of coils, thus eliminating alignment problems and simplifying the circuitry involved. Additionally, the implantable device may be made smaller and lighter in weight by eliminating a coil that was employed in many prior art devices. The invention also avoids mutual coupling problems experienced by prior art systems that required separate sets of coils for energy transmission and data telemetry. These and various other characteristics and advantages of the present invention will be readily apparent to those skilled in the art upon reading the following detail description and referring to the accompanying drawings.

BRIEF DESCRIPTION OF THE DRAWINGS

Other objects and advantages of the invention will become apparent upon reading the following detailed description and upon reference to the accompanying drawings in which:

FIG. 6 is a timing diagram showing waveforms generated by various components and circuits of the control system shown in FIG. 5.

FIG. 7 is an enlarged view of a portion of a waveform shown in FIG. 6.

DETAILED DESCRIPTION OF THE PREFERRED EMBODIMENT

Figure 1:
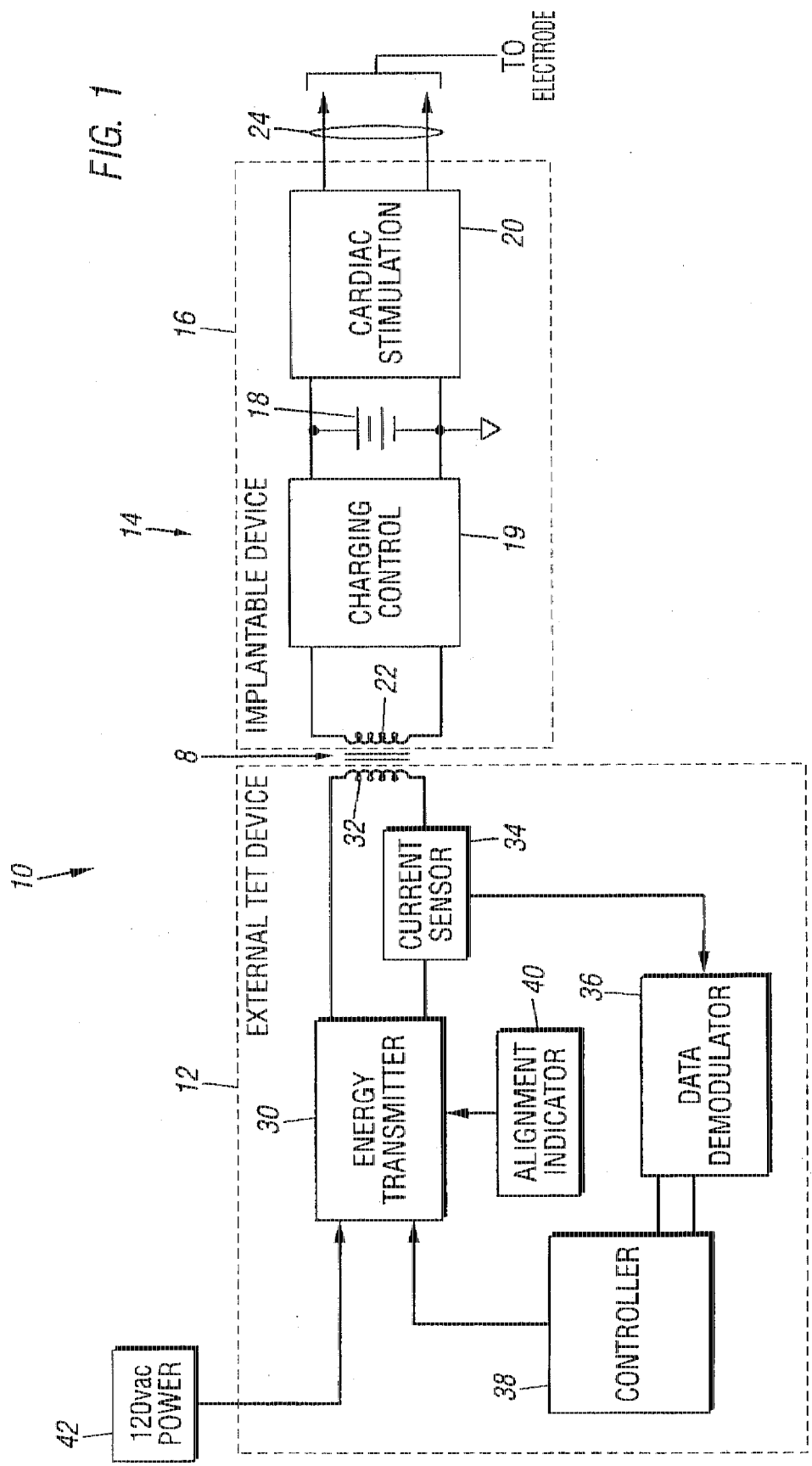
FIG. 1 is a schematic block diagram of the data communication and charging control system of the present invention as may be employed to recharge batteries in an implantable medical device.

Referring now to FIG. 1, the data communication and charging control system 10 of the present invention generally includes a transcutaneous energy transmission (TET) device 12 and an implantable, battery-powered medical device 14. To aid in the understanding of the detailed description which follows, a general overview of system 10 is first described, followed by a description of the various system components and interconnections. After the components have been thus, identified and described, a detailed description of the operation of the data communication and charging control system 10 is provided.

System Overview

Implantable medical device 14 may be any bioimplantable device such as a cardiac pacemaker, a defibrillator, a drug infusion and dispensing system, as examples. For purposes of describing the preferred embodiments of the data communication and charging control system, the invention will be described as employed in a defibrillator. it being understood, however, that the invention may likewise be employed in any of a variety of other implantable medical devices.

Referring still to FIG. 1, implantable defibrillator 14 includes a housing or "can" 16, preferably made of titanium or stainless steel, which houses rechargeable battery 18, charging control circuitry 19, cardiac stimulation circuitry 20, and coil 22. Implantable defibrillator 14 is surgically implanted beneath the skin 8 in the chest or the pectoral region of the patient. In general, and as understood by those skilled in the art, battery 18 powers cardiac stimulation circuitry 20 which, according to a predetermined protocol, stimulates the heart by delivering electrical pulses of appropriate magnitude and duration to one or more implanted electrodes (not shown), interconnected with control circuitry 20 by electrical leads 24. Cardiac stimulation circuitry 20 may comprise any of a variety of pulse generation circuits including, for example, those disclosed in U.S. Pat. Nos.

5,318,596, 5,040,534 and 4,830,006, the disclosures of which are incorporated herein by reference. Battery 18 may be any type of rechargeable battery suitable for use in an implantable device. Preferably, however, battery 18 is a lithium battery as disclosed in commonly assigned U.S. Pat. No. 5,411,537, the disclosure of which is incorporated by reference. Charging control circuitry 19 couples between coil 22 and battery 18 and generally senses the level of charge of battery 18 and communicates that information to TET device 12 in order to control the delivery of energy to battery 18.

Referring still to FIG. 1, TET device 12 is powered by a conventional 120 VAC power source 42 and generally includes energy transmitter 30, coil 32, current sensor 34, data demodulator 36, controller 38 and alignment indicator 40. In some applications coil 32 may be housed separately from the rest of the TET device components. In a general sense, current sensor 34, data demodulator 36 and controller 38 receive encoded voltage and current data transmitted by implantable device 14 to control energy transmitter 30. Alignment indicator 40 functions to ensure proper alignment of coil 32 and coil 22 during charging periods. Charging efficiency is much higher when the coils are properly aligned. A preferred technique for providing an indication of proper alignment is disclosed in the commonly assigned copending U.S. patent application Ser. No. 08/482,786, the disclosure of which is incorporated herein by this reference.

Coils 22 and 32 may be any coils capable of transmitting energy transcutaneously between external TET device 12 and implantable device 14. Coil 32 preferably is pancake shaped with high inductance and low AC resistance. Coil 22 preferably is light weight and small to allow for small implantable device size.

When it is desirable to charge battery 18 in implantable device 14, external coil 32 is positioned on the external surface of the patient's skin proximally to the implanted device 14 and delivers energy to recharge battery 18 transcutaneously by means of electromagnetic induction between coil 32 in external TET device 12 and coil 22 in implantable device 14. Charging control circuitry 19 in implantable device 14 samples battery voltage and current and transmits that data to TET 12 via coils 32, 22 in order to control the energy transmission between TET device 12 and implantable device 14. The battery voltage is indicative of the level of charge of battery 18. More specifically, to transmit the sampled data, charging control circuitry 19 alternately disconnects and reconnects the battery from the charging circuit in a predetermined manner, causing the current in the coil 32 of TET device 12 to change in response to the change in load across coil 22. This current charge in coil 32 is detected by the current sensor 34 and transmitted to data demodulator 36. As explained in more detail below, data demodulator 36 decodes voltage and current values and communicates these values to controller 38 which, pursuant to predetermined parameters, control the power output of the transmitter 30.

TET Device 12

Figure 2:
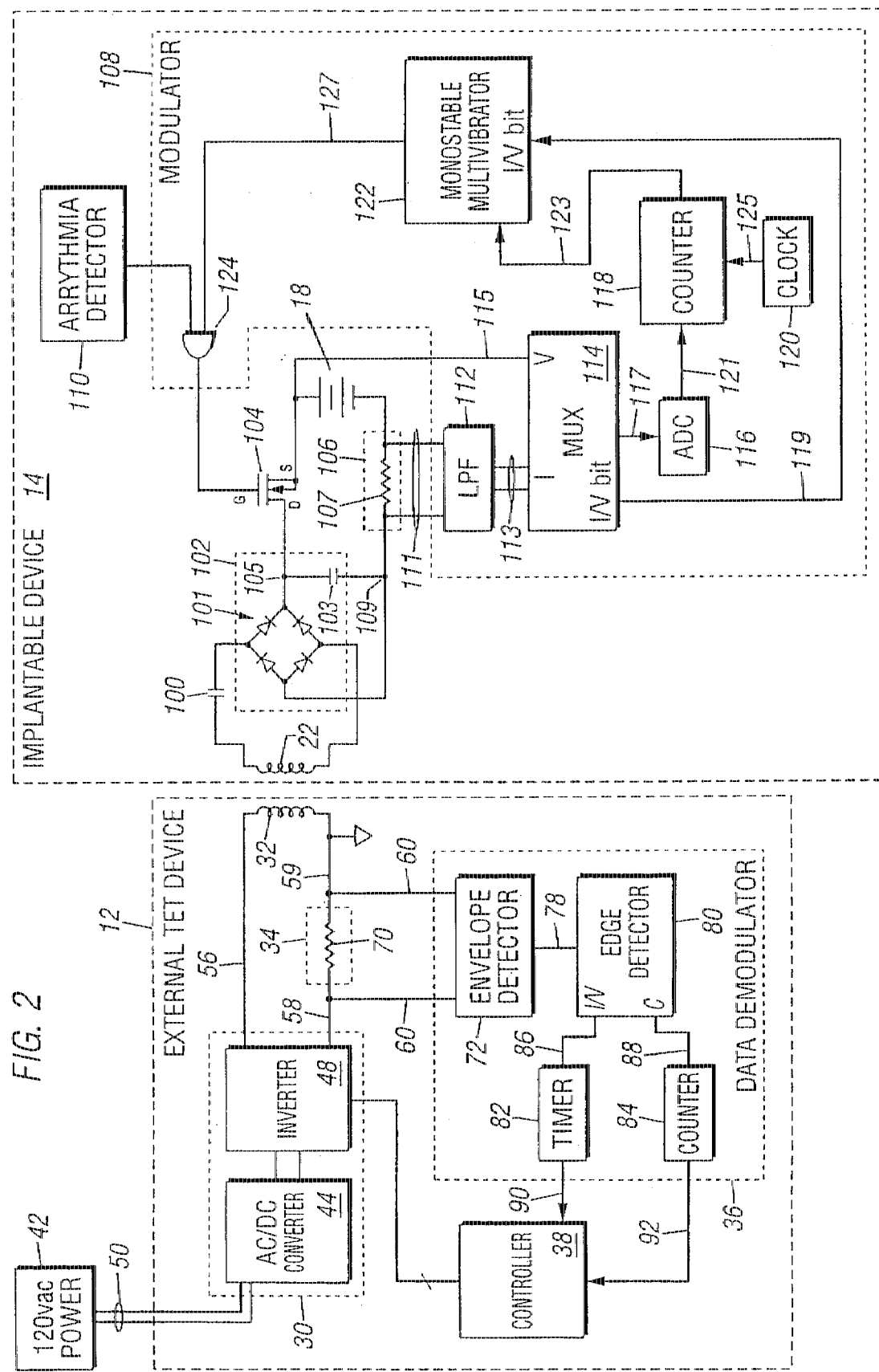
FIG. 2 is a schematic block diagram providing additional details of the control system shown in FIG. 1.

Referring now to FIG. 2, energy transmitter 30 includes alternating current-to-direct current (AC/DC) converter 44 and inverter 48. Power is supplied to AC/DC converter 44 from 120 volt AC power source 42 via conductors 50. AC/DC converter 44 converts the AC power to a DC voltage appropriate for transcutaneous energy transmission. A multitude of known circuit implementations may be employed for AC/DC converter. The DC output from AC/DC converter 44 is transmitted to inverter 48 by conductors 52. Inverter 48 converts the regulated DC voltage to a sinusoidal current that is conducted through coil 32 via conductors 56, 58 at times when inverter 48 is enabled by controller 38. The output voltage of AC/DC converter 44 also supplies DC power to controller 38 by conventional conductors (not shown).

Inverter 48 includes a power resonant circuit which provides AC current to coil 32 as described in copending U.S. patent application Ser. No. 08/482,786. When current is conducted through coil 32, it electromagnetically induces a current in coil 22 of implantable device 14 (FIG. 1). Alignment indicator 40 (FIG. 1) is also coupled to inverter 48 as described in patent application Ser. No. 08/482,786, but is not shown in FIG. 2 for the sake of clarity.

Referring still to FIG. 2, current sensor 34 comprises a current sensing, low resistance resistor 70 that is connected between coil 32 and energy transmitter 30 by conductors 58, 59. Resistor 70 preferably has a resistance of approximately 0.5A or less. When coil 32 is energized, the voltage across resistor 70 will be proportional to the current through the resistor, and thus proportional to the current through the coil 32. The output from current sensor 34 is transmitted to data demodulator 36 by conductors 60. Other conventional current sensors capable of sensing current and providing an output signal representative of the magnitude of the current may likewise be employed.

Data demodulator 36 generally includes envelope detector 72, edge detector 80, timer 82 and counter 84, all of which are conventional analog and digital designs well known to those skilled in the art. Envelope detector 72 is employed to sense the change in magnitude of the current that is conducted through coil 32 and to generate a square wave pulse in response to changes in the current's magnitude. The output of envelope detector 72 is coupled to edge detector 80 by line 78. Edge detector 80 includes two discrete outputs. A first output, designated as I/V, is employed to distinguish voltage values from current values and generates very short duration pulses at the leading and trailing edges of each of the pulses received by edge detector 80 from envelope detector 72. A second output, designated as C provides a time interval to counter 84 so that the magnitude of the current or voltage value being transmitted can be decoded. The outputs I/V and C of edge detector 80 are coupled to timer 82 and counter 84 via lines 86, 88, respectively. Timer 82 and counter 84 are coupled to controller 38 by lines 90, 92, respectively. Controller 38 preferably comprises a microprocessor capable of generating a pulse width modulation (PWM) control signal, although other forms of circuitry, such as analog or digital circuitry can be used in place of a microprocessor. A preferred microprocessor that is characterized by having a high energy efficiency which is useful in the present application is that described in U.S. Pat. No. 4,404,972, the disclosure of which is hereby incorporated by this reference.

Implantable Device 14

Referring momentarily again to FIG. 1, energy provided transcutaneously to battery 18 by TET device 12 for powering cardiac stimulation circuitry 20 is controlled by charging control circuitry 19, best described with reference to FIG. 2. As shown in FIG. 2, charging control circuitry 19 generally includes tuning capacitor 100, rectifier 102, switch 104, current sensor 106, modulator 108 and arrhythmia detector 110. For clarity, cardiac stimulation circuitry 20 (FIG. 1) of implantable device 14 is not depicted in FIG. 2.

Rectifier 102 is provided to convert the AC current induced in coil 22 to DC for charging battery 18 through switch 104 which, as controlled by modulator 108, is closed during charging. Rectifier 102 preferably comprises a full-wave bridge rectifier 101 and capacitor 103. Capacitor 103 preferably functions as a low-pass filter to obtain a low ripple DC current for battery 18. Series capacitor 100 connects between rectifier bridge 101 and coil 22 to form a resonant circuit in conjunction with coil 22. The resonant circuit comprising capacitor 100 and coil 22 preferably is tuned to the frequency of the AC current in the coil 32 of TET device 12, which preferably is approximately a 5 KHz charging carrier frequency.

Switch 104 controls the flow of charging current to battery 18 and preferably comprises a metal oxide field effect transistor (MOSFET). In accordance with normal convention, MOSFET 104 includes a source terminal S, drain terminal D, and gate terminal G. The MOSFET's source terminal S connects to battery 18 and the drain terminal D connects to terminal 105 of rectifier 102. The gate terminal G preferably couples to an output of modulator 108 which controls the opening and closing of switch 104 as described below in more detail.

Current sensor 106 preferably connects between battery 18 and terminal 109 of rectifier 102. Any of a variety of current sensors could be employed as sensor 106. In the preferred embodiment described herein, current sensor 106 includes a low resistance resistor 107 (approximately 0.5 ohm) coupled in series with battery 18 such that the current flowing through battery 18 will be conducted through resistor 107. The value of current sensed by current sensor 106 is transmitted to modulator 108 by conductors 111.

As shown in FIG. 2, modulator 108 generally includes low pass filter (LPF) 112, multiplexer (MUX) 114, an analog-to-digital converter (ADC) 116, counter 118, clock 120, programmable monostable 122 and AND gate 124. The output of AND gate 124 connects to the gate terminal G of MOSFET switch 104 and operates to turn on and off MOSFET switch 104 at the appropriate times as detailed below.

Low pass filter 112 connects to current sensor 106 by conductors 111 and removes high frequency noise from the current signal transmitted by current sensor 106. Any conventional LPF may be employed. The filtered analog current signal is transmitted to current input I of MUX 114 by conductors 113. MUX 114 also includes a voltage input V which senses the voltage of battery 118 via conductor 115. MUX 114 multiplexes the analog voltage and current signals into a single analog output which is transmitted to ADC 116 along line 117. MUX 114 also includes a digital output "I/V bit" which, coincident to the output of an analog signal to ADC 116, provides programmable monostable 122 with a digital signal on line 119 indicating whether the simultaneously-transmitted analog signal on line 117 represents a current or voltage value. MUX 114 may be any suitable mutiplexer capable of multiplexing the received current and voltage signals and providing an I/V bit coincident with the analog signal being transmitted.

ADC 116 is preferably a conventional solid state device and receives the multiplexed voltage/current analog signal from MUX 114 and converts the value received to a digital signal which is transmitted to counter 118 via line 121. Counter 118 may be any suitable up or down counter of the type that is initially loaded with a count value and that then counts up to or down from that count value and outputs a roll-over bit upon completion of the programmed count. In this application, the initial count value is loaded into counter 118 from ADC 116. A clock 120 preferably connects to counter 118 by line 125 and provides a train of regularly-timed pulses for counting by counter 118. At the start and at the completion of its count, counter 118 transmits a pulse to the enable input of monostable multivibrator 122 along line 123.

Monostable multivibrator 122 receives the digital signal from counter 118 and the I/V bit from MUX 114 and, depending upon whether the signal is a current value or voltage value, generating pulses to AND gate 124 of pre-programmed durations and intervals along control line 127. The output of arrhythmia detector 110 is gated with the output of programmable monostable 122 at AND gate 124. When no arrhythmia is detected, the output from arrhythmia detector will be a logic high to allow charging and data telemetry to take place. Arrhythmia detector 110 may be any conventional detector capable of sensing an arrhythmia condition and providing a digital output signal of such an occurrence, such as that described in Chapter 4 ("Tachyarrhythmia Sensing and Detection" by Walter H. Olson) of *Implantable Cardioverter Defibrillator* (editor: Igor Singer; Publisher: Futura Publishing Company, Inc. of Armonk N.Y. copyright; 1994), Chapter 4 being incorporated herein by reference.

System Operation

According to the principles of the present invention, telemetry of battery voltage and current levels occurs during transcutaneous charging of the battery by TET device 12. Charging current in TET device 12, thus, is not stopped in order to transmit telemetry from the implantable device 14 to the external TET device 12. The general theory of operation provides that the voltage across and current through TET coil 32 is, in part, a function of the current in coil 22 of implantable device 14 which, in turn, is proportional to the load across coil 22. In this manner, the current in coil 32 of the external TET device 12 can be altered by opening and closing switch 104 which effectively disconnects load from internal coil 22. The data modulator 108 in implantable device 14 senses battery voltage and current at regular intervals (once every minute or two) and encodes those values in digital form to open and close switch 104 in a predetermined manner. The change in current through coil 32 of TET device 12 that occurs when the load is connected and momentarily disconnected in implantable device 14 is sensed by the data demodulator 36 in TET device 12 which extracts the encoded battery voltage and current values and transmits those values to controller 38. Depending on those values, the output power of inverter 48 is regulated by controller 38.

Figure 3:
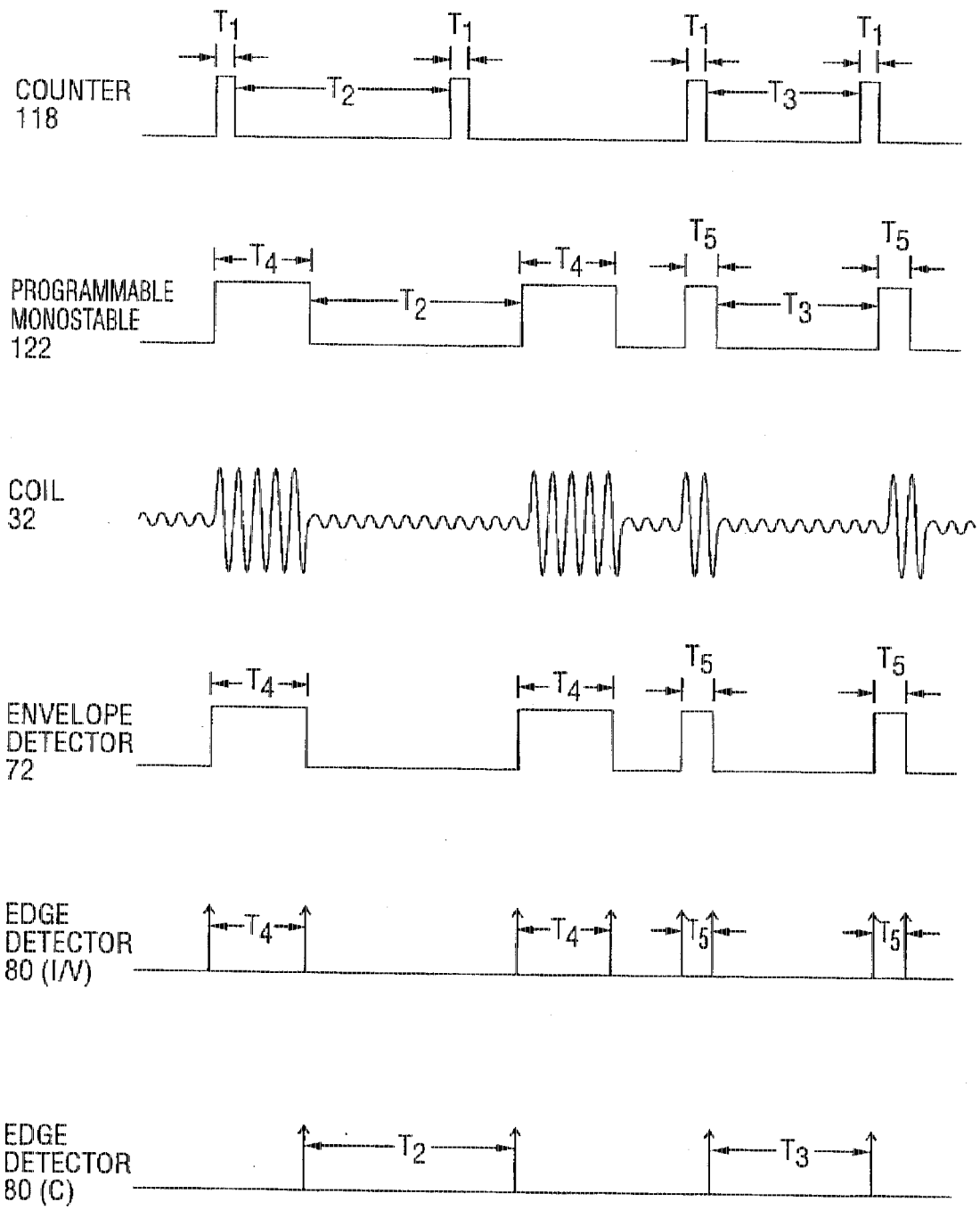
FIG. 3 is a timing diagram showing the waveforms generated by various components and circuits of the control system shown in FIG. 2.

The details of operation of system 10 are best understood with reference to FIG. 2 in conjunction with the timing diagram of FIG. 3 which shows the waveforms generated by various system components. As explained above, the output of ADC 116 is a digital signal representing battery current and voltage values multiplexed together. The digital signal is input or "loaded" into counter 118 and represents what will be referred to herein as the "count value." For purposes of this explanation, counter 118 will be described as an up counter that counts pulses received from clock 120 from zero up to the count value. As one skilled in the art will understand, various types of counters and counting protocols may be used without departing from the principles of the present invention. Referring still to FIGS. 2 and 3, counter 118 generates a pulse having width T1 at the beginning of the count and another pulse of width T1 when the count value has been reached. The time between the beginning and ending pulses represents the voltage or current value then being transmitted. For example, if the measured voltage is 3.6 volts, the counter is loaded with a count value by ADC 116 reflecting the 3.6 volts, and then begins counting from zero up to the count value. The time between the falling edge of the first T1 pulse and the rising edge of the next T1 pulse is defined as period T2 represents the voltage value. Following the transmission of T1 pulses for the voltage value, a value representative of the sensed current will be loaded as the count value into counter 118 by ADC 116. Counter 118 will then generate pulses of width T1 at the beginning and end of the count. The period between these pulses, depicted as T3, represents the sensed current value. These counter pulses of width T1 are transmitted along control line 123 to monostable multivibrator 122 which generates a corresponding pulse for each pulse received from counter 118. The pulse width of each pulse generated by monostable multivibrator 122 is predetermined and is dependent upon whether the data being transmitted is a voltage or a current value. Although other relative pulse widths can be used, in the preferred embodiment, the pulses representing voltage values are at least three times as great in duration (pulse width) as the pulses representing current values. The monostable multivibrator 122 differentiates the values received from counter 118 (and thus itself generates pulses of appropriate width) by means of its receipt of the I/V bit from MUX 114 on control line 119. For example, a logic high on the I/V bit signifies a voltage value has been transmitted to monostable multivibrator 122, while a logic low on the I/V bit signifies a current value has been transmitted. The I/V bit is set coincident with the count value being loaded into counter 118.

Accordingly, when the pulses from counter 118 and the appropriate I/V bit are input into monostable multivibrator 122, monostable multivibrator 122 generates corresponding pulses shown in FIG. 3. The pulses representing voltage values have pulse widths of T4 while pulses of width T5 represent current values. The leading edge of the initial t4 or T5 pulse in each pair of pulses coincide with the leading edges of initial T1 pulses from counter 118. The leading edge of the second T4 or T5 pulse in each pulse pair occurs T2 or T3 seconds following the falling edge of the initial T4/T5 pulse. Pulses T4 and T5 are transmitted to AND gate 124 sequentially in order to open and close switch 104 for short periods of time to transmit the encoded voltage and current values to TET device 12. As will be understood by one skilled in the art, the pulses T4 and T5 are applied to the gate G of the MOSFET causing the switch 104 to open.

As previously discussed, the current through the coil 32 in TET device 12 is, in part, dependent upon the load across coil 22 in implantable device 14. Thus, when switch 104 opens during the duration of pulses T4 and T5, the magnitude of the current in coil 32 generally increases significantly as shown in FIG. 3. One of ordinary skill in the art, however, will recognize that, in fact, current in coil 32 may increase or decrease in response to switch 104 depending on the tuning between the external and internal resonant circuits. The change in coil current magnitude occurs during the T4 or T5 pulses from monostable multivibrator 122. Current sensor 34 in TET device 12 senses the current in coil 32 and transmits a current signal to envelope detector 72 which then detects the change in the current magnitude and provides an output pulse that generally corresponds to that generated by monostable multivibrator 122 with voltage pulses of duration T4 and current pulses of duration T5. Envelope detector 72 thus recovers the monostable multivibrator's output signal as shown in FIG. 3. The output from envelope detector 72 is input into edge detector 80 which generates a narrow pulse for each rising and falling edge of the pulses generated by envelope detector 72 at output I/V. The time between these pulses will thus be equal to T4 (for voltage values) or T5 (for current values). The narrow pulses generated by edge detector 80 are applied to timer 82 from I/V terminal via signal line 86. Timer 82 receives the pulses output from output I/V of edge detector 80 and measures the time between each pair of pulses (i.e., the time between the rising and falling edges of T4 and T5) and outputs to controller 38 either a logic high (for voltage values) or a logic low (for current values). Thus, timer 82 provides an indication to controller 38 of the type of value (current or voltage) being monitored.

Edge detector 80 also preferably generates a narrow pulse at output terminal C coincident with the falling edge of a first pulse of a pair of pulses received from envelope detector 80, and a second narrow pulse on the rising edge of the next pulse of the received pair. Thus, edge detector 80 generates a pair of pulses at terminal C reflecting the end of a first pulse and the beginning of a second pulse. These pulses are then loaded as count values in counter 84 which calculates the time (T2 or T3) between these two pulses. The output of the counter 84 is a digital value that is correlated by controller 38 with the logic level low or high signal received from timer 82. More specifically, if the logic level is high, the controller will recognize that data value T2 (generated originally by counter 118) is being received from counter 84 and representative of battery voltage. Similarly, upon receipt of a logic low from timer 82, controller 38 will assume the value from counter 84 is a current value T3. The controller 38 uses the voltage and current values to control the power output of transmitter 30 such that the battery charging current is regulated and then terminated upon the battery becoming fully charged.

The embodiment of the invention described above permits simultaneous data telemetry and battery charging. Another presently-preferred embodiment of the invention is described below with reference to FIGS. 4–6 and is designed to transmit data only when the charging has been halted. This alternative embodiment includes many of the same or similar components as those previously described. Thus, in the description that follows, identical reference numerals are used to identify common or similar elements.

Figure 4:
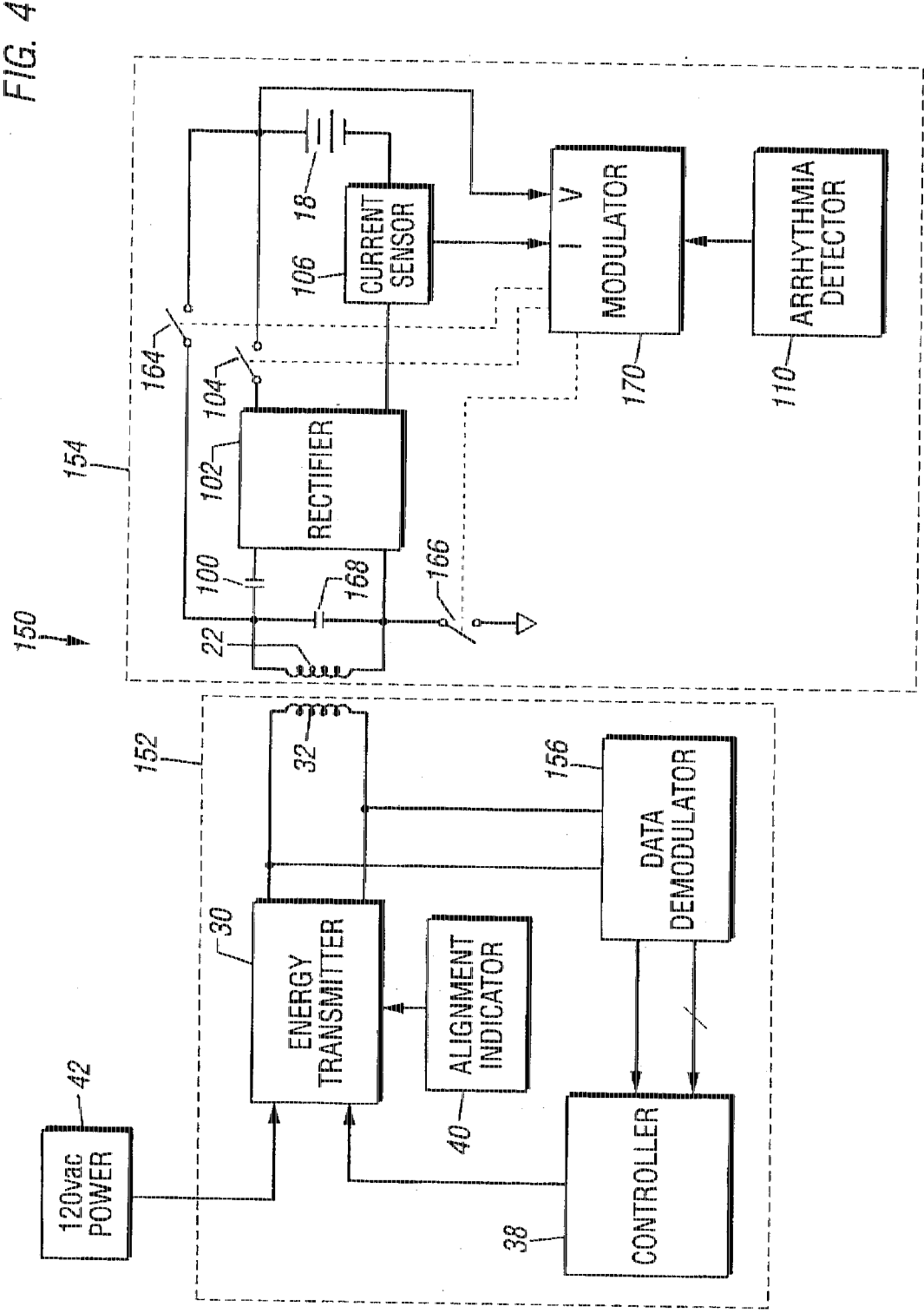
FIG. 4 is a schematic block diagram of an alternative embodiment of the data communication and charging control system of the present invention.
Figure 5:
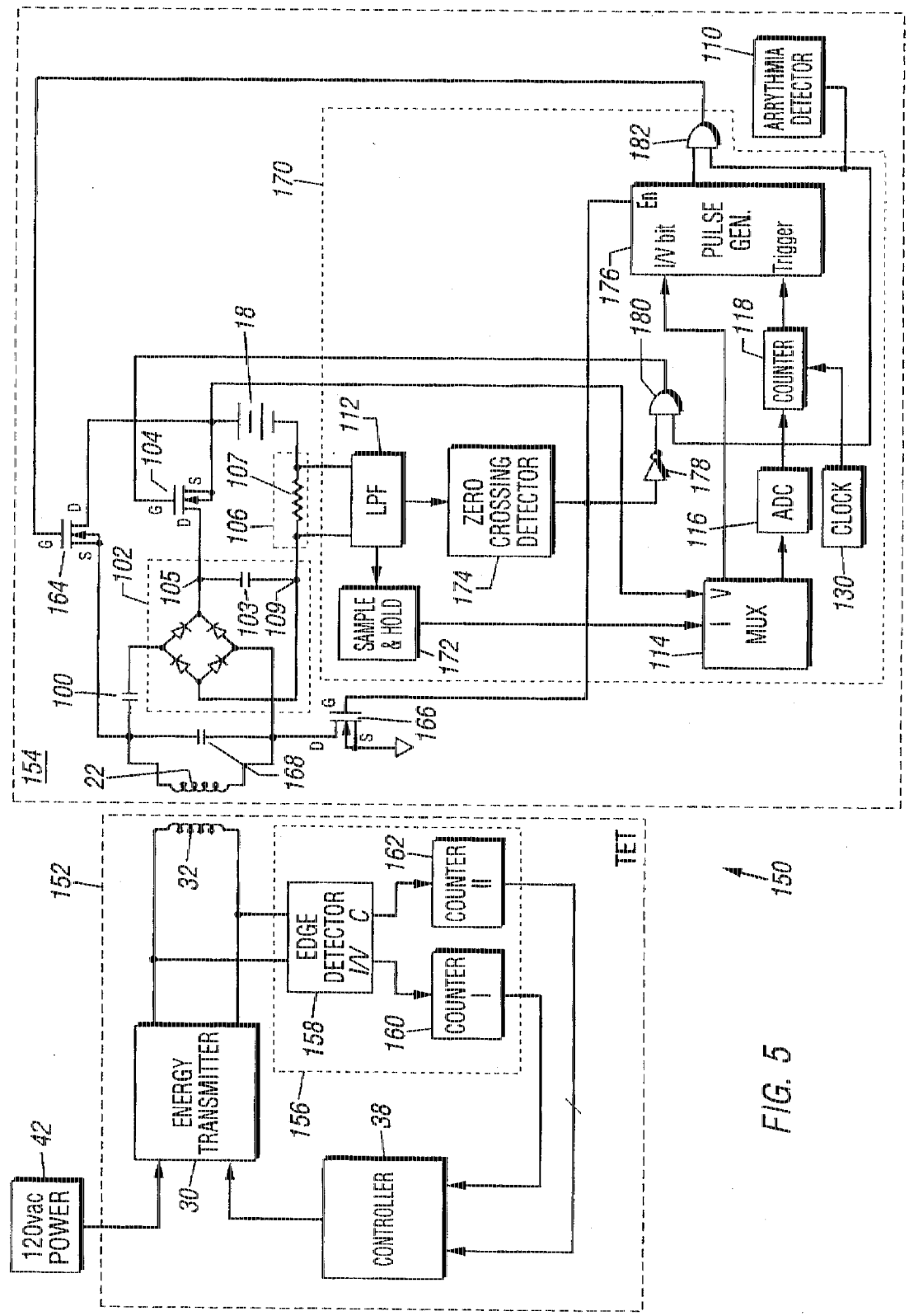
FIG. 5 is a schematic block diagram showing additional details of the control system of FIG. 4.

Referring now to FIG. 4, data communications and charging control system 150 includes TET device 152 and implantable medical device 154. TET device 152 generally includes energy transmitter 30, coil 32, controller 38 and alignment indicator 40 all as previously described. In addition, TET device 152 includes a data demodulator 156. As best shown in FIG. 5, the demodulator 156 includes edge detector circuitry 158, and a pair of counters 160, 162. Edge detector 158 is similar to edge detector 80 previously described. Likewise, counters 160, 162 are conventional counters, such as counter 118 described above. As will be explained in more detail momentarily, data demodulator 156 receives the encoded voltage and current values transmitted by implantable device 154, decodes those values, and provides them to controller 38 for use in controlling energy transmitter 30.

Referring again to FIG. 4, implantable device 154 includes battery 18, coil 22, capacitor 100, rectifier 102, switch 104, current sensor 106 and arrhythmia detector 110, all as previously described. Implantable device 154 further includes switches 164, 166, capacitor 168 and modulator 170. Switches 164, 166 are preferably MOSFET's such as that used for switch 104 in the preferred embodiment. As mentioned above, control system 150 halts battery charging to permit data telemetry. Thus, when the TET device 152 requires battery voltage and current information from the implantable device 154, the TET device 152 turns off the charging current to coil 32. When this occurs, current sensor 106 in implantable device 154 detects the absence of current through coil 22, and causes modulator 170 to open switch 104, to close switch 166, and to toggle switch 164 on and off to modulate battery voltage and current information in a manner described in greater detail below. During charging, switch 104 is closed, and switches 164 and 166 are open. Arrhythmia detector 110 disables both data telemetry and battery charging upon the onset of arrhythmia by disabling switch 104.

Modulator 170 is best understood with reference to FIG. 5. As shown therein, modulator 170 includes LPF 112, MUX 114, ADC 116, counter 118, and clock 130, all as previously described. Additionally, modulator 170 employs a sample and hold device 172, a zero crossing detector 174, and a pulse generator 176. Current sensor 106 includes a low voltage resistor 107, previously described, and provides an analog signal representing battery current to LPF 112 which extracts high frequency noise and charging carrier frequency. LPF 112 provides a filtered signal to both sample and hold device 172 and zero crossing detector 174.

Sample and hold device 172 is a convention solid state component which samples and then holds the current value input from LPF 112 until the next value is sampled. The held value is output to the "I" input of MUX 114. The frequency of the sample and hold circuit is preferably one sample per second, although other sampling rates can be employed. It will be understood that, although the charging current detected by current sensor 106 goes to zero when TET device 152 terminates energy transmission in order to receive telemetry, sample and hold device 172 retains and outputs the last sampled current value to MUX 114, despite the absence of battery charging current at that moment.

MUX 114 receives a current input from sample and hold 172 and a voltage input from battery 18 and multiplexes the battery voltage and current values into a single analog output. This signal is then digitized by the ADC 116 and input into counter 118 as the count value, all as previously described.

Referring now to FIGS. 5 and 6, counter 118 is an up counter which generates a pulse at the beginning and end of its count, as best shown in FIG. 6. The time between the pairs of pulses (from the falling edge of the first pulse to the rising edge of the second pulse) from counter 118 represents either voltage or current. As shown in FIG. 6, the pair of pulses representing a voltage value are separated by a time T1, while a current value is represented by pulses separated by time T2. In control system 150 of FIGS. 4–6, modulator 170 encodes a value as voltage or current by employing pulse generator 176 which generates a different number of pulses, depending upon whether the value it has received from counter 118 is a voltage or a current value. If the value input from counter 118 represents a voltage, pulse generator 176 generates a series of three short-duration pulses for each pulse input from counter 118. If the pulse received from counter 118 represents a current value, pulse generator 176 generates a single output pulse. Pulse generator 176 is a conventional solid state element having a trigger input that is coupled to the output of counter 118 and an I/V bit input which receives an input from MUX 114 so that pulse generator 176 can identify the value received from counter 118 as either a voltage or a current value and thereby generate the proper number of output pulses. The output of pulse generator 176 is gated through AND gate driver 182 with the output of arrhythmia detector 110. The output from AND gate driver 182 controls switch 164. If no arrhythmia is detected, the output from arrhythmia detector 110 is a logic level high such that each pulse from pulse generator 176 momentarily closes switch 164.

As stated above, data telemetry is initiated by the TET device 152 terminating charging current through coil 32. When this occurs, the current conducted through resistor 107 of current sensor 106 becomes essential zero which is detected by the zero crossing detector 174. The output of zero crossing detector 174 is a logic level that indicates whether the input is substantially zero, or is some higher value that would indicate that charging current is still flowing through coil 22 and that it is thus not time to provide telemetry to TET device 152. In the embodiment shown, the output of zero crossing detector 174 will be a logic level high when current is conducted through current sensor 106 and a logic level low when its input goes to zero. Thus, when battery charging is stopped, the zero crossing detector 174 will output a low logic level signal which is inverted by inverter 178 and gated through AND gate driver 180 with the output of arrhythmia detector 110. The output of AND gate driver 180 will thus open switch 104 (if no arrhythmia is detected) so as to disconnect battery 18 from the charging circuit and permit encoded voltage and current data to be transmitted to TET device 152 via switch 164 and coils 22, 32. Switch 166 connects coil 22 and capacitor 168 to battery ground comprising a resonant circuit when switch 164 is turned on.

More particularly, switch 164 is turned on and off with each pulse output from pulse generator 176 (when no arrhythmia is detected). With switch 104 disabled or off during data telemetry, battery 18 is coupled through switch 164 to the inductor and capacitor network formed by coil 22 and capacitor 168, Thus, each pulse generated by pulse generator 178 creates a corresponding analog pulse across primary coil 32 in TET device 152 as shown in FIG. 6. This waveform, which is received by edge detector 158, is a damped sinusoid signal, best shown in FIG. 7.

Referring again to FIG. 5, edge detector 158 includes two separate output terminals, terminal "C" for providing a value of the current or voltage sensed, and terminal "I/V" for providing output identifying the value as either a current or voltage magnitude. Additionally, edge detector 158 includes a comparator (not shown specifically) with a predetermined reference or trigger level, such as that represented in FIG. 7. Whenever the input to edge detector 158 exceeds the trigger level of the comparator, a narrow pulse is output from the edge detector's I/V terminal to counter 160. If the counter 160 receives a series of three pulses, then counter 160 will output a logic level that corresponds to voltage. If counter 160 instead receives a single input pulse, then counter 160 will output the opposite logic level so that controller 38 can differentiate between voltage values and current values that will be received from counter 162.

Referring again to FIG. 6, edge detector 158 will also generate a signal from output terminal C to be decoded to provide the current or voltage value sensed and transmitted by implantable device 154. More specifically, if edge detector 156 receives a series of three closely spaced sinusoids, it will output a single pulse from output C to counter 162 upon the detection of the third in the series of pulses, and will then generate a single output pulse upon detection of the first in the next series of three sinusoids, the period between these two pulses being T1 which represents the magnitude of battery voltage. Because the next sinusoidal waveforms it receives will be single pulses representing a current value, edge detector 156 will next output to counter 162 a single pulse for each sinusoid received, the time between those two pulses T2 representing the magnitude of the current as transmitted by implantable device 154.

While preferred embodiments of this invention have been shown and described, modifications thereof can be made by one skilled in the art without departing from the spirit or teaching of this invention. The embodiments described herein are exemplary only and are not limiting. Many variations and modifications of the system and apparatus are possible and are within the scope of the invention. Accordingly, the scope of protection is not limited to the embodiments described herein, but is only limited by the claims which follow, the scope of which shall include all equivalents of the subject matter of the claims.

We claim as our invention:

1. An implantable device, comprising:
   a battery capable of being recharged by a transcutaneous energy transmission device;
   a coil that selectively couples to said battery via a switch, said coil receiving energy from said transcutaneous energy transmission device for charging said battery;
   a current sensor coupled to said battery for detecting the amount of current flowing through said battery and for providing an output signal indicative of the current flowing through said battery;
   a multiplexing circuitry coupled to said battery for detecting voltage of the battery, said multiplexing circuitry also receiving the output signal indicative of the amount of current flowing through said battery, said multiplexer circuit generating a signal indicating either the amount of current through the battery or the voltage of the battery;
   output circuitry coupled to said multiplexing circuitry for receiving the signal from said multiplexing; and
   wherein said output circuitry selectively opens and closes said switch to transmit encoded signals through said coil to said transcutaneous energy transmission device indicative of the amount of current through said battery and the voltage of the battery.

2. A device as in claim 1, wherein a duration of time that the switch is opened by the output circuitry indicates whether the encoded signals represent current or voltage values.

3. A device as in claim 1, wherein the output circuitry includes an analog-to-digital converter connected to said multiplexer for receiving the signal indicative of the amount of current flowing through said battery or the voltage of the battery, said analog-to-digital converter converting said signal to a digital representation of the amount of current flowing through said battery, or the voltage of said battery.

4. A device as in claim 3, wherein the multiplexer circuitry alternatively transmits a voltage signal and a current signal to said analog-to-digital converter.

5. A device as in claim 4, wherein the output circuitry further includes a counter connected to said analog-to-digital converter for receiving said digital representation of the amount of current flowing through said battery or the voltage of said battery.

6. A device as in claim 5, wherein said counter loads said digital representation as a count value for the counter.

7. A device as in claim 6, wherein said output circuitry further includes a clock connected to said counter which causes said counter to count.

8. A device as in claim 7, wherein the counter generates a first output signal when the count begins.

9. A device as in claim 8, wherein the counter generates a second output signal when the count equals the count value.

10. A device as in claim 9, wherein the output circuitry further includes a programmable monostable circuit connected to said counter for receiving the first and second counter output signals.

11. A device as in claim 10, wherein the multiplexer circuit also generates a second signal indicating if the output signal to the analog-to-digital converter represents the amount of current flowing through the battery or the voltage of the battery.

12. A device as in claim 11, wherein the programmable monostable circuit also connects to said multiplexer circuit for receiving the second signal from said multiplexer circuit.

13. A device as in claim 12, wherein said programmable monostable circuit is connected to said switch to open and close said switch.

14. A device as in claim 13, wherein the programmable monostable circuit generates a first pulse in response to the first signal from said counter, and generates a second pulse in response to the second signal from said counter, and wherein the width of said pulses is based upon the second signal from said multiplexer circuit to indicate if the pulse represents a current value or a voltage value.

15. A device as in claim 14, wherein the time period between said pulses defines the magnitude of the current or voltage value.

16. A device as in claim 1, wherein said switch comprises a MOSFET device which includes a source terminal, a drain terminal and a gate terminal, and said output circuitry couples to said gate terminal to control current flow through said MOSFET between the source terminal and the drain terminal.

17. A device as in claim 1, further comprising means for closing said switch to permit charging of the battery, and for selectively opening said switch to transmit encoded signals.

18. A device as in claim 1, further comprising means for selectively closing said switch to transmit encoded signals and for opening said switch to permit charging of said battery.

19. A device as in claim 18, further comprising a sample and hold circuit coupled between said current sensor and said multiplexer circuit for storing a sensed current value in the event that no current is subsequently detected by the current sensor.

20. A device as in claim 19, wherein the sample and hold circuit generates a signal to said multiplexer circuit indicative of current flowing through said battery.

21. A device as in claim 20, wherein the output circuitry includes an analog-to-digital converter connected to said multiplexer for receiving the signal indicative of the amount of current flowing through said battery or the voltage of the battery, said analog-to-digital converter converting said signal to a digital representation of the amount of current flowing through said battery, or the voltage of said battery.

22. A device as in claim 21, wherein the multiplexer circuitry alternatively transmits a voltage signal and a current signal to said analog-to-digital converter.

23. A device as in claim 22, wherein the output circuitry further includes a counter connected to said analog-to-digital converter for receiving said digital representation of the amount of current flowing through said battery or the voltage of said battery.

24. A device as in claim 23, wherein said counter loads said digital representation as a count value for the counter.

25. A device as in claim 24, wherein said output circuitry further includes a clock connected to said counter which causes said counter to count.

26. A device as in claim 25, wherein the counter generates a first output signal when the count begins.

27. A device as in claim 26, wherein the counter generates a second output signal when the count equals the count value.

28. A device as in claim 27, wherein the output circuitry further includes a pulse generator connected to said counter for receiving the first and second output signal therefrom.

29. A device as in claim 28, wherein the multiplexer circuit generates an output signal to said pulse generator indicating if the first and second output signals from said counter relate to a current signal or to a voltage signal.

30. A device as in claim 29, wherein said pulse generator generates a number of pulses in response to said first and second signals from said counter, with the number of pulses determined by the status of the output signal from said multiplexer indicating if the first and second output signals from said counter relate to a current signal or to a voltage signal.

31. A device as in claim 30, wherein the pulse generator generates three pulses in response to each of said first and second signals from said counter if the output signal from said multiplexer circuit indicates the counter signals represent a voltage value.

32. A device as in claim 30, wherein the pulse generator generates one pulse in response to each of said first and second signals from said counter if the output signal from said multiplexer circuit indicates the counter signals represent a current value.

33. A device as in claim 18, further comprising a second switch coupled between said battery and said coil, and wherein said second switch is closed to permit charging of said battery and opened during periods when encoded signals are transmitted to said transcutaneous energy transmission device.

34. A device as in claim 33, further comprising a zero crossing detector coupled to said current sensor, wherein said zero crossing detector generates an output signal when the current flowing through said battery drops to zero.

35. A device as in claim 34, further comprising means responsive to the output signal from said zero crossing detector for opening said second switch.

36. A device as in claim 34, further comprising means responsive to the output signal from said zero crossing detector for enabling said output circuitry to transmit encoded signals to said transcutaneous energy transmission device.

37. A transcutaneous energy transmission system for simultaneously recharging a battery in an implanted device while providing encoded signals indicative of the voltage charge on the battery, comprising:
 an external transmission device which includes;
  a coil;
  a current sensor coupled to said coil for sensing current through the coil;
  detection circuitry coupled to said current sensor for detecting said encoded signal in said sensed current and in response generating a pulse;
  a timer coupled to said detection circuitry for measuring pulse duration; and
  a counter coupled to said detection circuitry for measuring time between pulses;
 an implantable device powered by said battery, said implantable device including:
  a coil for coupling to said coil in said external transmission device;
  a switch selectively coupling said coil to said battery;
  a current sensor coupled to said battery for detecting the amount of current flowing through said battery and for providing an output signal indicative of the current flowing through said battery;
  a multiplexing circuitry coupled to said battery for detecting voltage of the battery, said multiplexing circuitry also receiving the output signal indicative of the amount of current flowing through said battery, said multiplexer circuit generating a signal indicating either the amount of current through the battery or the voltage of the battery;
  output circuitry coupled to said multiplexing circuitry for receiving the signal from said multiplexing; and
  wherein said output circuitry selectively opens and closes said switch to transmit encoded signals through said coil to said transcutaneous energy transmission device indicative of the amount of current through said battery and the voltage of the battery.

38. A system as in claim 37, wherein the output circuitry provides a first and a second pulse of the same duration.

39. A device as in claim 38, wherein a duration of time that the switch is opened by the output circuitry indicates whether the encoded signals represent current or voltage values.

40. A system as in claim 39, wherein a pulse duration measured by said timer indicates if the pulse represents a current or voltage value.

41. A system as in claim 40, wherein a period between a first and second pulse indicates the magnitude of the current or voltage value.

42. A system as in claim 41, wherein the counter in said external transmission device comprises means for measuring the duration between pulses to determine the magnitude of the sensed current or voltage value.

43. A system as in claim 42, further comprising means for closing said switch to permit recharging of the battery and for opening said switch to enable transmission of encoded signals from the implanted device to said external device.

44. A transcutaneous energy transmission system for transmitting encoded signals indicative of the voltage charge on a battery during periods when battery recharging is interrupted, comprising:
 an external transmission device which includes;
  a coil;
  an edge detector coupled to said for detecting said encoded signal received by said coil and in response generating a pulse;
  a first counter coupled to said edge detector for measuring pulse duration; and
  a second counter coupled to said edge detector for measuring time between pulses;
 an implantable device powered by said battery, said implantable device including:
  a coil for coupling to said coil in said external transmission device;
  a switch selectively coupling said coil to said battery;
  a current sensor coupled to said battery for detecting the amount of current flowing through said battery and for providing an output signal indicative of the current flowing through said battery;
  a multiplexing circuitry coupled to said battery for detecting voltage of the battery, said multiplexing circuitry also receiving the output signal indicative of the amount of current flowing through said battery, said multiplexer circuit generating a signal indicating either the amount of current through the battery or the voltage of the battery;

output circuitry coupled to said multiplexing circuitry for receiving the signal from said multiplexing; and wherein said output circuitry selectively opens and closes said switch to transmit encoded signals through said coil to said transcutaneous energy transmission device indicative of the amount of current through said battery and the voltage of the battery.

45. A system as in claim 44, wherein said switch is closed to permit encoded signals to be transmitted by said implanted device to said external transmission device.

46. A system as in claim 45, further comprising a second switch coupled between said battery and said coil and wherein said second switch is closed to permit charging of said battery and opened during periods when encoded signals are transmitted to said transcutaneous energy transmission device.

47. A device as in claim 46, further comprising a zero crossing detector coupled to said current sensor, wherein said zero crossing detector generates an output signal when the current flowing through said battery drops to zero.

48. A device as in claim 47, further comprising means responsive to the output signal from said zero crossing detector for opening said second switch.

49. A device as in claim 47, further comprising means responsive to the output signal from said zero crossing detector for enabling said output circuitry to transmit encoded signals to said transcutaneous energy transmission device.

* * * * *